United States Patent
Carver, Jr. et al.

[11] Patent Number: 5,840,254
[45] Date of Patent: Nov. 24, 1998

[54] APPARATUS FOR MIXING FLUIDS FOR ANALYSIS

[75] Inventors: Edward Lawrence Carver, Jr.; David Charles DeCava, both of Oxford; Steven Skiptunas, Naugatuck, all of Conn.

[73] Assignee: CDC Technologies, Inc., Oxford, Conn.

[21] Appl. No.: 458,701

[22] Filed: Jun. 2, 1995

[51] Int. Cl.$^6$ .................................................. G01N 15/06
[52] U.S. Cl. ............................................ 422/68.1; 422/81
[58] Field of Search .................................. 436/51–53, 55, 436/49–50; 422/62–63, 68.1, 81

[56] References Cited

U.S. PATENT DOCUMENTS

| | | | |
|---|---|---|---|
| 3,793,587 | 2/1974 | Thom et al. | 324/71 |
| 3,810,010 | 5/1974 | Thom | 324/71 |
| 3,822,095 | 7/1974 | Hirschfeld | 356/39 |
| 3,836,849 | 9/1974 | Coulter et al. | 324/71 |
| 3,871,770 | 3/1975 | Von Behrens et al. | 356/103 |
| 3,900,290 | 8/1975 | Hornstra . | |
| 4,001,678 | 1/1977 | Berg | 324/71 |
| 4,014,611 | 3/1977 | Simpson et al. | 356/72 |
| 4,022,575 | 5/1977 | Hansen et al. | 23/230 R |
| 4,030,888 | 6/1977 | Yamamoto et al. . | |
| 4,036,062 | 7/1977 | Cruzan | 73/422 G |
| 4,050,904 | 9/1977 | Cramer . | |
| 4,146,604 | 3/1979 | Kleinerman | 424/3 |
| 4,165,484 | 8/1979 | Haynes | 324/71 |
| 4,198,160 | 4/1980 | Kachel et al. | 356/72 |
| 4,253,058 | 2/1981 | Kachel et al. | 324/71 |
| 4,323,537 | 4/1982 | Mody | 422/63 |
| 4,395,676 | 7/1983 | Hollinger et al. | 324/71.4 |
| 4,420,564 | 12/1983 | Tsuji et al. | 435/288 |
| 4,424,276 | 1/1984 | Clark et al. | 436/50 |
| 4,503,385 | 3/1985 | Haynes | 324/71.4 |
| 4,509,904 | 4/1985 | MacAskill et al. | 417/568 |
| 4,634,431 | 1/1987 | Whitney et al. | 604/155 |
| 4,683,212 | 7/1987 | Uffenheimer | 436/52 |
| 4,695,431 | 9/1987 | Farrell | 422/81 |
| 4,713,974 | 12/1987 | Stone | 73/864.23 |
| 4,908,187 | 3/1990 | Holmquist et al. | 422/81 |
| 4,920,060 | 4/1990 | Parrent et al. | 437/178 |

(List continued on next page.)

FOREIGN PATENT DOCUMENTS

| | | |
|---|---|---|
| 0 101 161 | 2/1984 | European Pat. Off. . |
| 0 107 333 | 5/1984 | European Pat. Off. . |
| 89/04961 | 6/1989 | European Pat. Off. . |

OTHER PUBLICATIONS

Fisher Scientific Catalog, 1988, pp. 1402–1403.
R. Hallawell et al., "An Evaluation Of The Sysmex NE–8000® Hematology Analyzer", *Am. J. Clin. Path*, Sep. 1991, vol. 96, pp. 594–601.
The Henley Group Inc., "The CELLECT™ Hematology Systems from Instrumentation Laboratory", 1986.
B. A. Payne et al., "Evaluation Of The TOA E–5000® Automated Hematology Analyzer", *Am. J. Clin. Path*, Jul. 1987, vol. 88, pp. 51–57.

*Primary Examiner*—Lyle A. Alexander
*Attorney, Agent, or Firm*—Cummings & Lockwood

[57] ABSTRACT

In an apparatus for fluid analysis, such as hematologic analysis, a plurality of reagent-mixture components are each injected by a respective pump through a valve matrix and into a flow-injection unit. The flow-injection unit defines a mixing chamber including a plurality of protuberances or nubs projecting inwardly toward the center of the chamber, and spaced relative to each other both axially and radially. As the reagent-mixture components are injected into the mixing chamber, the nubs agitate the fluid flow and create turbulence, thereby dispersing the reagent-mixture components and in turn mixing the components together to create a reagent mixture. The flow rates of the reagent-mixture components are adjusted in order to select the reagent-mixture ratio as the components are combined in the flow-injection unit to thereby create the selected reagent mixture. Upon passage through the flow-injection unit, the reagent mixture is injected into a sensing unit for analyzing a particle distribution of the mixture.

28 Claims, 4 Drawing Sheets

U.S. PATENT DOCUMENTS

| | | | |
|---|---|---|---|
| 4,948,565 | 8/1990 | Bemis et al. | 422/103 |
| 5,003,895 | 4/1991 | Talanker | 112/103 |
| 5,019,515 | 5/1991 | Gisin et al. | 436/52 |
| 5,030,002 | 7/1991 | North, Jr. | 356/73 |
| 5,092,989 | 3/1992 | Steen | 210/85 |
| 5,134,079 | 7/1992 | Cusack et al. | 436/53 |
| 5,180,677 | 1/1993 | Di Ianni et al. | 436/17 |
| 5,187,673 | 2/1993 | Carver, Jr. et al. | 364/555 |
| 5,223,398 | 6/1993 | Kortright et al. | 435/7.24 |
| 5,256,374 | 10/1993 | De Silva et al. | 422/80 |
| 5,260,027 | 11/1993 | Kuroda | 422/81 |
| 5,316,725 | 5/1994 | Carver, Jr. et al. | 422/61 |
| 5,627,041 | 5/1997 | Shartle | 422/50 |

APPARATUS FOR MIXING FLUIDS FOR ANALYSIS

FIELD OF THE INVENTION

The present invention relates to apparatus and methods for fluid analysis, and more particularly, to controlling fluid flow and mixing fluids in such apparatus and methods.

BACKGROUND OF THE INVENTION

Automated apparatus and methods for fluid analysis, such as hematologic analysis, typically pump a sample containing the particles suspended in a dispersion through a particle analyzer which detects differences in electrical, optical, chemical or other characteristics of the particles, and generates signals having characteristics relating to the differences. The signals are in turn transmitted to a processor for determining the parameters of the particle distributions.

Automated hematologic analysis typically involves mixing within a cuvette or other mixing vessel a whole blood sample with several reagent-mixture components, such as diluent, to create a reagent mixture which facilitates cell discrimination and identification. The reagent mixture is then pumped from the cuvette through a particle analyzer which detects the size (volume) and/or opacity of the blood cells by electrical or optical differences. The blood cells are detected or counted for a period of time sufficient to gather data for analysis, and data points are then stored and analyzed in a processor. The data may then be displayed in the form of a two-dimensional or three-dimensional histogram.

As a result of the reagent-mixing process in the cuvette or other mixing vessel and other inefficiencies in fluid transportation, prior art apparatus for hematologic and other fluid analyses generally use a substantially greater volume of blood or other sample fluid than the particle analyzers require for complete analysis. Accordingly, a substantial portion of the samples are typically discarded as waste. These inefficiencies lead to additional costs and inconvenience.

In addition, the mixing cuvette or other mixing vessel and related fluid-handling components, such as fluid conduits, valves, etc., require gravity and/or a controlled ambient pressure to mix the various reagent-mixture components, thus preventing the use of such apparatus in gravity-free applications and on moving vehicles, such as submarines, airplanes, ships, and land-based vehicles.

Moreover, once a reagent-mixture is made in a mixing cuvette or other mixing vessel, the mixture typically cannot be changed. Thus, for example, if a blood-cell abnormality is detected and it is necessary to change the dilution or mixture ratio of the reagent mixture to further assess the abnormality, the original reagent mixture must be discarded and another sample batch prepared, thus leading to sample waste, inconvenience and delays in obtaining analysis results.

In hematologic analysis, when the reagent-mixture components are combined in a mixing cuvette or other mixing vessel with lytic reagents, they are generally not immediately uniformly distributed to the blood cells. For example, there is typically a higher concentration of lytic reagents in the portion of the cuvette or vessel where the reagents are introduced. As a result, the lytic reagents have a varying effect on the blood cells throughout the sample batch and, accordingly, certain cells receive a higher gradient of lytic shock than do others. This uneven gradient of lytic shock typically results in insufficient separation in the blood cells under-exposed to lytic reagents, and damage and possible destruction of cells over-exposed to lytic reagents.

It is an object of the present invention to overcome the drawbacks and disadvantages of prior art apparatus and methods for fluid and/or particle analysis.

SUMMARY OF THE INVENTION

The present invention is directed to an apparatus and method for fluid analysis, such as hematologic analysis, of reagent mixtures having a plurality of reagent-mixture components. A plurality of pumps are independently operable for pumping the reagent-mixture components, and a flow-injection unit is coupled through a valve matrix to the pumps for receiving the reagent-mixture components. The flow-injection unit injects at least one reagent-mixture component into a stream of at least one other reagent-mixture component to mix the components and create a selected reagent mixture. A control unit controls operation of the pumps to adjust the flow rates of the reagent-mixture components, and in turn adjust the reagent-mixture ratio upon injection and mixture of the components in the flow-injection unit. The reagent mixture is in turn pumped from the flow-injection unit and injected into a sensing unit for analyzing a particle distribution of the reagent mixture.

One advantage of the present invention, is that the reagent-mixture components are injected and mixed in the flow-injection unit en route to the sensing unit for particle analysis. Accordingly, the mixing cuvettes or like mixing vessels employed in prior art apparatus are obviated, and the inefficiencies associated with such apparatus that mix an entire sample batch prior to beginning analysis are avoided. Yet another advantage of the present invention is that the mixture ratio of the reagent mixture may be adjusted at any time, either before or during particle analysis, by adjusting the flow-rate ratio of the reagent-mixture components.

Other advantages of the present invention will become apparent in view of the following detailed description and accompanying drawings.

DETAILED DESCRIPTION

Figure 1:
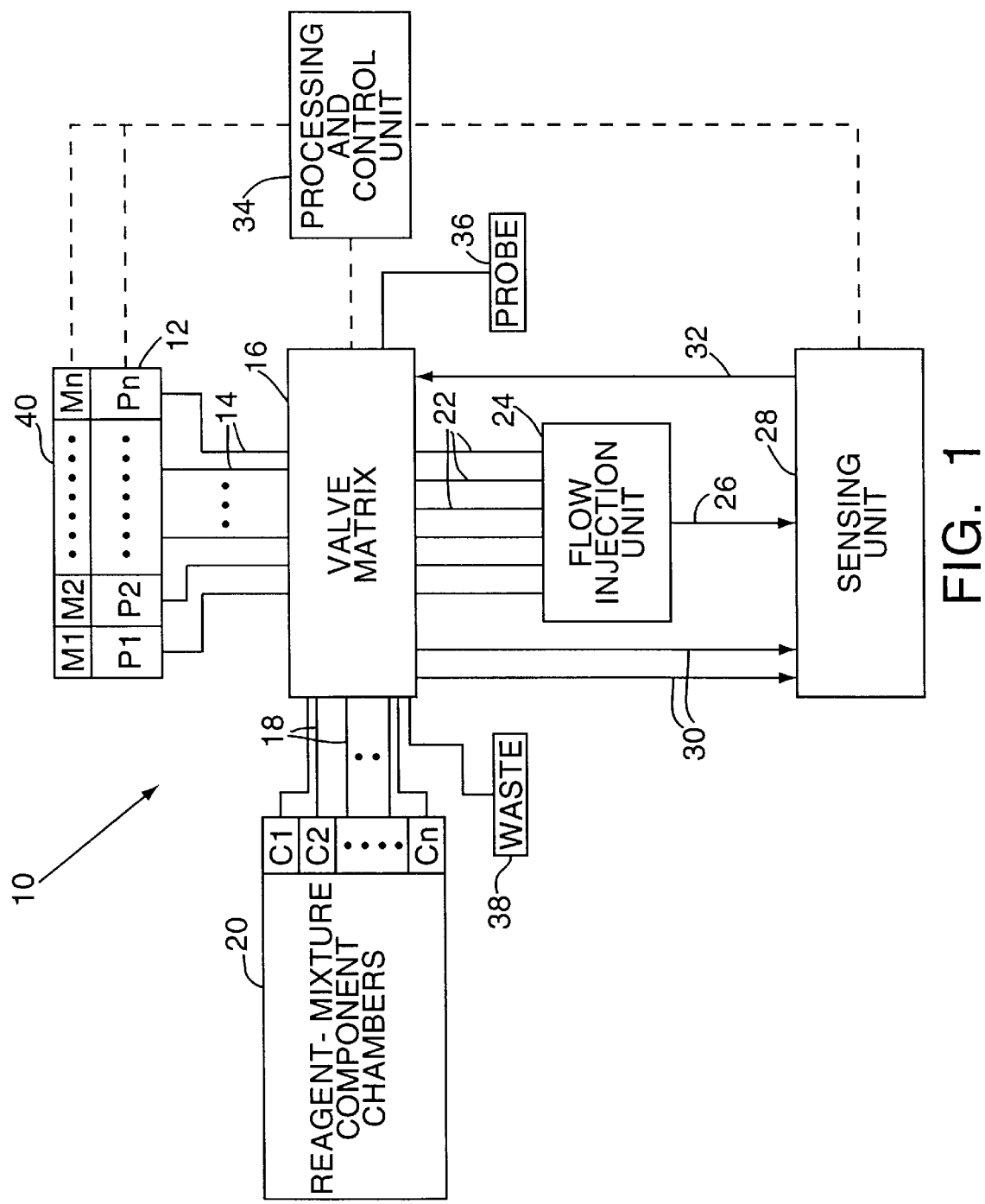
FIG. 1 is a block diagram of an apparatus and flow-injection system embodying the present invention.

In FIG. 1, an apparatus and flow-injection system embodying the present invention is indicated generally by the reference numeral 10. The apparatus 10 is adapted for automated hematologic analysis; however, as will be recognized by those skilled in the pertinent art, the present invention may equally be employed and/or adapted for numerous other types of fluid and/or particle analysis. For example, the apparatus of the present invention may also be employed for chemical analysis, including blood chemical analysis, such as glucose, BUN, etc.

The apparatus 10 comprises a plurality of pump units 12, indicated schematically in FIG. 1 as P1, P2 . . . Pn, which are coupled in fluid communication through a plurality of pump lines 14 to a valve matrix 16. The valve matrix 16 is of a type known to those of ordinary skill in the pertinent art and connects the various fluid-handling components of the apparatus in fluid communication with each other to control the direction and flow of reagent-mixture components and other fluids, if necessary. The valve matrix 16 is in turn connected through a plurality of lines 18 to a bank of reagent-mixture component chambers 20, indicated schematically in FIG. 1 as C1, C2 . . . Cn. Each chamber 20 is adapted to receive a respective reagent-mixture component, such as a whole blood sample, diluent, lysing reagent, or diluted blood sample. If necessary, one or more chambers 20 may contain other fluids to be used, for example, to rinse or wash conduits and other fluid-handling components of the apparatus.

The valve matrix 16 is also connected through a plurality of injection/aspiration lines 22 to a flow-injection unit 24 for introducing at least one reagent-mixture component into a stream of at least one other reagent-mixture component in order to immediately thoroughly and uniformly mix the components and create a reagent mixture, as is described in detail below. The flow-injection unit 24 is coupled through a reagent-mixture injection line 26 to a sensing unit 28 for detecting differences in electrical, optical, chemical or other characteristics of particles in the reagent mixture, and generating signals having characteristics relating to the differences.

One or more secondary injection/aspiration lines 30 are coupled between the valve matrix 16 and sensing unit 28 for pumping other fluids to the sensing unit, including, for example, diluent sheaths surrounding the reagent-mixture stream. One or more return lines 32 are also coupled between the sensing unit 28 and valve matrix 16 for receiving fluids from the sensing unit, including, for example, the reagent mixture and diluent sheath surrounding the reagent mixture, as is also described further below.

As also shown in FIG. 1, a processing and control unit 34 is coupled to each of the pump units 12, the valve matrix 16 and sensing unit 28 to control operation of each component, analyze the data, and provide analysis results. The sensing unit 28 is preferably of the type disclosed in U.S. Pat. No. 5,380,491, entitled "Apparatus For Pumping And Directing Fluids For Hematology Testing", and U.S. application Ser. No. 08/370,023, filed Jan. 9, 1995, which is a divisional of U.S. Pat. No. 5,380,491, both of which are assigned to the Assignee of the present invention, and are hereby expressly incorporated by reference as part of the present disclosure.

A reagent mixture is injected through the line 26 into a counting orifice (not shown) of the sensing unit 28, and a first diluent sheath is simultaneously injected through one of the secondary lines 30 on the inlet side of the counting orifice surrounding the reagent-mixture stream. Another secondary line 30 is coupled on one end to the outlet side of the counting orifice, and is coupled on the other end through the valve matrix 16 to a respective chamber 20 containing diluent for aspirating a second stream of diluent surrounding the reagent-mixture stream on the outlet side of the counting orifice. As disclosed in the above-mentioned patent, the sensing unit 28 preferably includes means for preventing intermixing of the sample stream and sheath fluids, including inlet ports for the secondary lines 30 carrying the diluent which are each oriented substantially tangential to a contiguous surface defining either the inlet or outlet chamber, respectively, of the sensing unit.

In hematologic analysis, the sensing unit 28 includes a transducer for counting the white blood cells and measuring their volume (size) and/or opacity by electrical or optical differences. The blood cells are counted for a period of time to gather sufficient data for analysis, and the data is stored and analyzed in the processing and control unit 34 to determine the parameters of the constituent subpopulations of the reagent-mixture sample. The processing and control unit 34 is preferably constructed and operates in accordance with the apparatus and method disclosed in U.S. Pat. Nos. 5,187,673 and 5,349,538, both of which are assigned to Edward L. Carver, Jr., and are hereby expressly incorporated by reference as part of the present disclosure.

As will be recognized by those skilled in the art, the sensing unit may be changed as necessary to perform the desired analysis. For example, for chemical analysis, such as blood-chemical analysis, the sensing unit may employ an optical transducer or like means for sensing photometric changes in the reagent mixture. The optical transducer measures the optical characteristics of the reagent mixture (e.g., absorbance, reflection and scattering) to determine the chemical constituents of the reagent mixture and their relative quantities.

As also shown in FIG. 1, the apparatus 10 may further comprise a probe 36 coupled to the valve matrix 16 for aspirating the various fluids through the valve matrix and introducing the fluids into the various reagent-mixture component chambers 20. A waste chamber 38 is also coupled to the valve matrix 16 for receiving the fluids after passage through the sensing unit 28, and any other fluids in the apparatus to be discarded as waste. As will be recognized by those skilled in the art, if desired, the fluids aspirated through the probe 36 may be aspirated directly into the flow-injection unit and introduced into the reagent-mixture stream so as to bypass the reagent-mixture component chambers 20. Such fluids may also be aspirated into a pump or pump line, and in turn injected by the respective pump into the flow-injection unit so as to likewise bypass the reagent-mixture component chambers 20.

Each of the pump units 12 is preferably a positive-displacement pump, such as a syringe pump, as shown, for example, in U.S. Pat. No. 5,380,491. As shown in FIG. 1, each pump unit 12 is preferably independently driven by a respective pump motor 40, illustrated schematically as M1, M2 . . . Mn, and each pump motor is coupled to the processing and control unit 34. Accordingly, each pump unit 12 can be independently actuated and controlled by the processing and control unit 34, to in turn independently control the flow rates of the fluids being injected or aspirated by the pumps. Each pump motor 40 may be a step motor, or other DC or AC motor with proper feedback and electronic control in order to precisely control actuation of the motor and respective pump, and in turn precisely control the volumes and flow rates of the fluids being pumped.

As will be recognized by those skilled in the pertinent art, it may be desirable to employ a transmission system with suitable speed-changing gears coupled between two or more pump units and a common pump motor, in order to reduce the number of motors, while permitting independent control of pump flow rates. Where independent control of certain pumps is unnecessary, and to save costs, it may likewise be desirable to employ a common pump motor for two or more pumps, as shown, for example, in U.S. Pat. No. 5,380,491.

In order to minimize fluid waste and in turn further minimize the volume of reagent-mixture components necessary for analysis, the valves employed in the valve matrix 16 preferably exhibit zero dead volume. A preferred type of zero dead volume valve is disclosed in co-pending patent application Ser. No. 08/385,145, filed Feb. 7, 1995, entitled "Valve Assembly", which is assigned to the Assignee of the present invention, and is hereby expressly incorporated by reference as part of the present disclosure.

Figure 2:
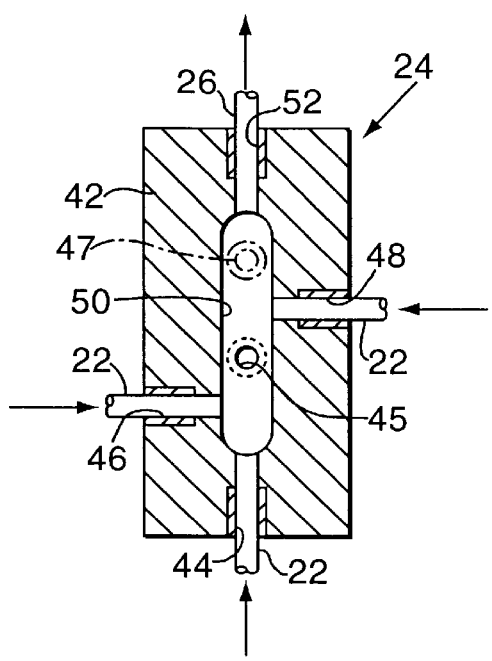
FIG. 2 is a somewhat schematic, cross-sectional view of a first embodiment of a flow-injection unit of the apparatus of FIG. 1.
Figure 3:
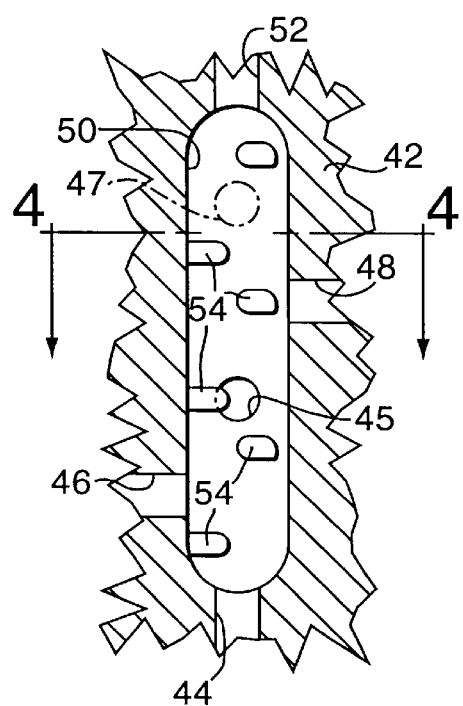
FIG. 3 is a somewhat schematic, cross-sectional view of the mixing chamber of the flow-injection unit of FIG. 2.
Figure 4:
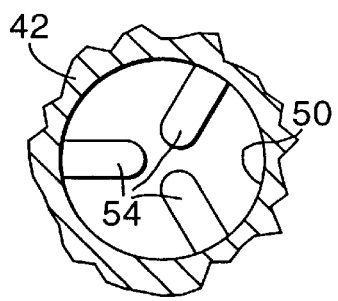
FIG. 4 is a cross-sectional view of the mixing chamber taken along line 4–4 of FIG. 3.

Turning to FIGS. 2–4, a first embodiment of the flow-injection unit 24 comprises a mixing block 42 defining a plurality of inlet ports 44, 45, 46, 47 and 48 coupled in fluid communication with an internal mixing chamber 50. As shown in FIG. 2, each inlet port 44–48 is also coupled to a respective flow-injection line 22 for receiving a respective reagent-mixture component and introducing the same into the mixing chamber 50 to immediately uniformly and thoroughly mix a plurality of components and create a selected reagent mixture. The mixing block 42 also defines an outlet port 52 coupled on one end in fluid communication with the mixing chamber 50 downstream of the inlet ports for receiving the reagent mixture, and coupled on the other end to the reagent-mixture injection line 26 for injecting the same through the sensing chamber, as is described further below. As will be recognized by those skilled in the pertinent art, although FIG. 2 shows five inlet ports, other inlet ports may be added to accommodate additional reagent-mixture components.

As shown in FIGS. 3 and 4, the internal configuration of the mixing chamber 50 is designed to immediately thoroughly and uniformly mix the various reagent-mixture components to create selected reagent mixtures. Accordingly, the mixing block 42 further includes a plurality of protuberances or nubs 54 projecting inwardly from the cylindrical wall of the chamber. As shown in FIG. 3, the nubs 54 are spaced relative to each other in the elongated direction of the chamber (i.e., each nub is located either upstream or downstream from the next nub). As shown in FIG. 4, the nubs 54 project inwardly toward the center of the chamber, and are also spaced radially relative to each other. In the exemplary embodiment, each nub 54 is angularly spaced and staggered from the next in the elongated direction of the chamber.

Accordingly, as the reagent-mixture components are introduced into the mixing chamber 50, as indicated by the arrows in FIG. 2, the nubs 54 agitate the fluid flow and create turbulence within the chamber, which in turn disperses the reagent-mixture components and causes them to immediately thoroughly and uniformly mix together and create the desired reagent mixture. Then, as the reagent mixture is injected through the outlet port 52 and into the smooth-walled, reagent-mixture injection line 26, the fluid flow returns to a substantially laminar state for injection through the counting orifice in the sensing unit 28. The substantially laminar flow of the reagent mixture through the flow-injection lines and sensing unit is facilitated by the steady-state flow generated by the positive displacement pumps, and the configuration of the sensing unit, as further described in U.S. Pat. No. 5,380,491 incorporated above.

In the operation of the apparatus of the present invention for hematologic analysis, a whole blood sample is introduced into the probe 36 of FIG. 1 by connecting a pump unit 12 through the valve matrix 16 to the probe, and controlling the respective pump motor 40 to aspirate a predetermined volume of whole blood sample through the probe. The blood sample may then either be injected by the respective pump into an available reagent-mixture component chamber 20 to hold the sample, or may be retained within the respective pump line 14 to await further processing. Each of the other reagent-mixture component chambers 20 may contain another respective reagent-mixture component, such as a lysing reagent (e.g., lysing reagents A, B, etc.) and diluent. Each of the chambers can also be coupled through the valve matrix 16 to the probe 36 to aspirate the reagent-mixture components into the component chambers. Preferably, the component chambers 20 also each include an access opening to pour or otherwise introduce the reagent-mixture components into the component chambers.

Exemplary reagent-mixture components and the preferred methods for employing these components are disclosed in U.S. Pat. No. 5,262,329, entitled "METHOD FOR IMPROVED MULTIPLE SPECIES BLOOD ANALYSIS", dated Nov. 16, 1993, U.S. Pat. No. 5,316,725, entitled "REAGENT SYSTEM FOR THE IMPROVED DETERMINATION OF WHITE BLOOD CELL SUBPOPULATIONS", dated May 31, 1994, and U.S. Pat. No. 5,316,951, entitled "METHOD FOR THE IMPROVED DETERMINATION OF WHITE BLOOD CELL SUBPOPULATIONS", dated May 31, 1994, which are each assigned to Edward L. Carver, Jr., and are hereby expressly incorporated by reference as part of the present disclosure.

The processing and control unit 34 has a database of information pertaining to the predetermined reagent-mixture ratios for selected species (e.g., human, dog, cat, rat, mouse, horse, cow, rabbit, monkey, pig, goat, bird or bird-type, etc.), and if desired, for selected conditions associated with each species. Accordingly, an operator may input through a keyboard or other input device for the control unit 34 the particular animal species, or if necessary, a specific reagent-mixture ratio that may not otherwise be in the database. The processing and control unit 34 is responsive to this input to control a plurality of the pump motors 40 to drive the respective pump units 12 to aspirate from the reagent-mixture chambers 20 into each pump a predetermined volume of a respective reagent-mixture component corresponding to the selected reagent-mixture ratio. The control unit 34 also aspirates a predetermined volume of diluent from a diluent chamber 20 into a respective pump unit 12 for injecting the diluent sheath surrounding the reagent-mixture stream.

In the event that the motors 40 are step motors, the control unit 34 can precisely measure the volume of each reagent-mixture component aspirated by counting the steps of the respective pump motor. If the motor is another type of AC or DC motor, a suitable encoder or like means may be employed to precisely track the rotational or drive position of the pump motor, and thus the volume and flow rate of the fluid being injected or aspirated by the respective pump.

The processing and control unit 34 operates the pump motors 40 to simultaneously inject or, if desired, aspirate each of the selected reagent-mixture components into the flow-injection unit 24 to thoroughly and uniformly mix the components and create the selected reagent mixture. In accordance with the invention, the flow rate of each reagent-mixture component is set by the control unit 34 so that the flow-rate ratio is the same as the desired reagent-mixture ratio. For example, if the desired reagent-mixture ratio is 1000 $\mu$l diluent:60 $\mu$l lysing reagent A:20 $\mu$l blood, then the flow rates for these selected reagent-mixture components are set at a ratio of 1000:60:20, respectively. In the embodiment of the present invention illustrated, the flow-rate ratios are set by adjusting the speed of each pump motor to achieve the respective flow rates and thereby achieve the selected mixture ratio.

If desired, however, different size positive-displacement pumps, such as syringe pumps, may be employed, wherein the relative sizes are selected to achieve the desired flow-rate and reagent-mixture ratios. For example, to achieve a 1000:60:20 ratio, 1000 $\mu$l, 60 $\mu$l and 20 $\mu$l pumps may be employed, and the three pumps may be driven at the same speed by a common motor, or may be independently driven at the same speed by three motors. Alternatively, any combination of different size positive-displacement pumps and independent and/or common drive motors may be used in like manner to achieve the desired flow-rates and reagent-mixture ratios.

The selected reagent-mixture components are then simultaneously introduced into the flow-injection unit 24 at the selected flow-rate ratio. As shown in FIG. 2, the inlet ports 45–48 are each oriented substantially perpendicular to both the axis or elongated direction of the mixing chamber 50 and first inlet port 44. As a result, the reagent-mixture components are simultaneously introduced into the mixing chamber in different directions. This, in combination with the effect of the nubs 54 creates turbulence and enhances the immediate thorough and uniform dispersion of each reagent-mixture component into and within the reagent-mixture stream.

Accordingly, the reagent-mixture components are simultaneously introduced and mixed in the flow-injection unit 24, and the resultant reagent mixture is in turn injected through the reagent-mixture injection line 26 and into the sensing unit 28. The substantially steady-state flow of the positive-displacement pumps introducing the reagent mixture through the flow-injection unit 24 and into the sensing unit 28, in combination with the smooth-walled configuration of the flow-injection line 26 and sensing unit, facilitates the return of the reagent-mixture stream to a substantially laminar flow as it enters the sensing unit. The control unit also simultaneously injects a first diluent sheath surrounding the reagent-mixture stream on the inlet side of the counting orifice, and injects or aspirates a second diluent sheath on the outlet side of the counting orifice through the secondary lines 30 to facilitate maintaining a uniform, concentric and steady-state flow of reagent mixture through the counting orifice. Upon passage through the sensing unit, the reagent mixture is aspirated into the return line 32 by an additional pump unit 12 and is ultimately discharged into the waste chamber 38.

As will be recognized by those skilled in the pertinent art, the reagent-mixture components may be introduced into the flow-injection unit and combined with each other in the reagent-mixture stream by injecting or aspirating (i.e., pushing or pulling) the fluids as desired through the flow-injection unit. For example, certain reagent-mixture components may be injected, whereas one or more other components may be aspirated through the flow-injection unit, or if desired, all fluids may be introduced by aspiration into the flow-injection unit, depending upon the desired configuration of the pump units and their connections to the flow-injection unit.

One advantage of the apparatus of the present invention, is that the reagent-mixture components are simultaneously introduced and mixed to create the reagent mixture "on the fly" as the components are pumped en route to the sensing unit. Accordingly, the mixing cuvettes or like mixing vessels used in prior art apparatus are obviated, and the inefficiencies in fluid transportation associated with such cuvettes avoided. As a result, a substantially lesser volume of sample fluid (e.g., blood sample), along with lesser volumes of other reagent-mixture components (e.g., lysing reagents) may be used in comparison to prior art apparatus. This is particularly the case if the valve matrix employs zero dead volume valves for controlling fluid flow, as described above.

Yet another advantage of the present invention, is that the mixture ratio of the reagent mixture may be adjusted at any time, either before or during analysis, by adjusting the flow-rate ratio of the reagent-mixture components, as described above. Thus, for example, if a blood-cell abnormality is detected during analysis, the control unit may be employed to adjust the flow rate of one or more reagent-mixture components, such as the diluent, to adjust the blood-dilution ratio, in order to further assess the abnormality. This is a significant advantage over prior art apparatus that prepare reagent-mixture batches in mixing cuvettes or other mixing vessels. In contrast to the present invention, the sample batches created in prior art apparatus cannot be adjusted once made, and often require that additional blood samples be taken or used to further assess abnormalities.

Yet another advantage of the present invention is that the reagent-mixture components are continually and simultaneously introduced into the mixing chamber of the flow-injection unit, which, in combination with the configuration of the mixing block, thoroughly and uniformly mix the components together in a reagent-mixture stream. As a result, a substantially even gradient of lytic shock is achieved, which in turn leads to effective separation of blood cells, and avoids the damage and/or destruction of cells and the insufficient separation of cells associated with an uneven gradient of lytic shock as can occur in prior art apparatus.

In addition, because the reagent-mixture components are combined "on the fly" in the flow-injection unit, as opposed to being first prepared in a mixing cuvette, the system may be sealed with respect to its environment, thus permitting operation in gravity-free applications. The apparatus of the invention may likewise be employed on moving vehicles, such as ships, submarines, airplanes, and land-based vehicles, without fluid spillage or other interruption in its operation. Moreover, because there is no need for a mixing cuvette or like mixing vessel, and due to the relatively small fluid volumes necessary for analyses, the apparatus of the present invention is particularly suited for small-scale applications or miniature versions for use in space or on moving vehicles.

Figure 5:
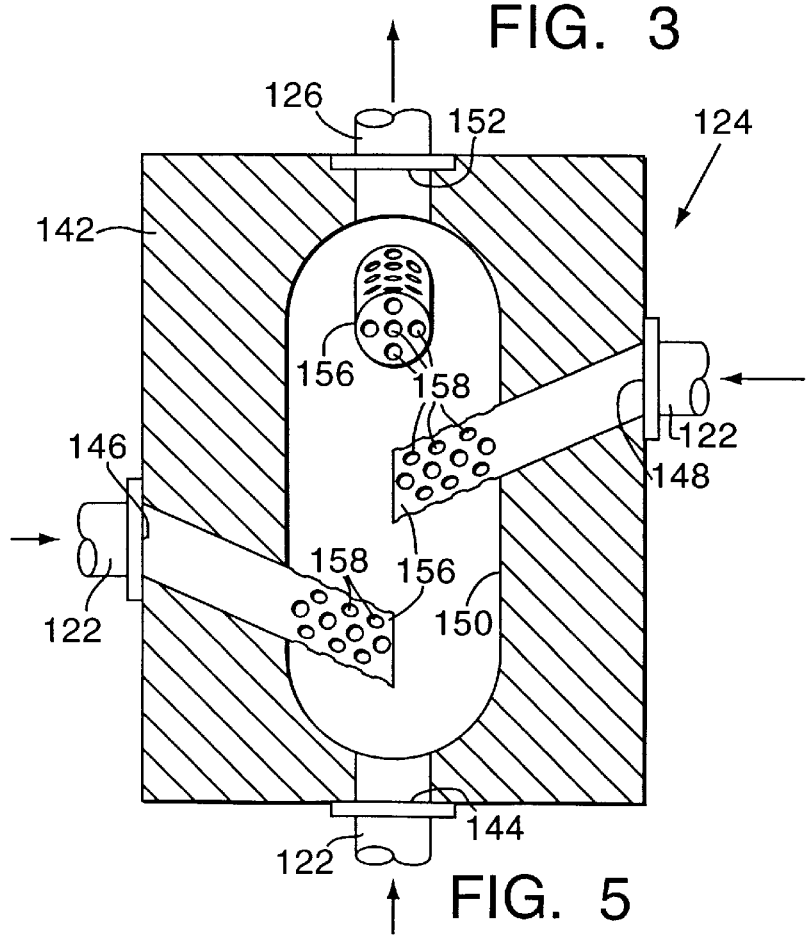
FIG. 5 is a somewhat schematic, cross-sectional view of another embodiment of a flow-injection unit for the apparatus of FIG. 1 having perforated injection tubes for diffusing the reagent-mixture components into the reagent-mixture stream.

In FIG. 5, another embodiment of the flow-injection unit is indicated generally by the reference numeral 124. Because many of the features of the flow-injection unit 124 are the same or similar to that of the flow-injection unit 24 described above, like reference numerals preceded by the numeral 1 are used to indicate like elements. The primary difference of the flow-injection unit 124 is that it includes a plurality of flow-injection tubes 156, each coupled on one end to a respective inlet port located on an elongated side of the mixing block 142, and projecting on the other end into the mixing chamber 150. Each injection tube 156 defines on its free end a plurality of perforations or apertures 158 spaced relative to each other and extending through the wall of the tube for introducing a respective reagent-mixture component into the mixing chamber 150.

As shown in FIG. 5, the perforated end of each tube 156 projects inwardly to the approximate center of the mixing chamber and is pointed generally toward the inlet end of the chamber, i.e., in an upstream direction. Accordingly, the reagent-mixture components introduced through the perforations 158 flow in an opposite or different direction than the reagent-mixture component introduced through the first inlet port 144, thus causing turbulence and facilitating the immediate thorough and uniform mixing of each component into the reagent-mixture stream. As also shown in FIG. 5, the injection tubes 156 are spaced relative to each other in the elongated direction of the mixing chamber (i.e., each tube is located either upstream or downstream from the next), and each tube is also spaced relative to the next radially. As will be recognized by those skilled in the pertinent art, if necessary, a plurality of protuberances or nubs as described above, or like means may be added for further agitating the fluid flow in the mixing chamber and thereby enhancing the dispersion of reagent-mixture components into the reagent-mixture stream.

Figure 6:
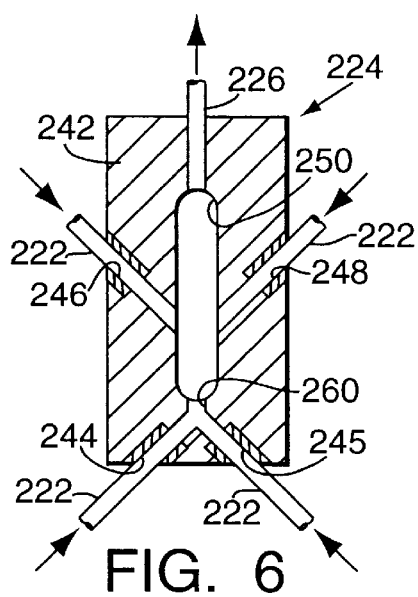
FIG. 6 is a somewhat schematic, cross-sectional view of another embodiment of a flow-injection unit for the apparatus of FIG. 1.

Turning to FIG. 6, another embodiment of the flow-injection unit is indicated generally by the reference numeral 224. Because many of the features of the flow-injection unit 224 are the same or similar to that of the flow-injection unit 24 described above, like reference numerals preceded by the numeral 2 are used to indicate like elements.

The primary difference of the flow-injection unit 224 in comparison to the unit 24 is that the inlet ports located on the elongated sides of the mixing block, shown typically at 246 and 248, are each oriented at an acute angle with respect to the axis or elongated direction of the mixing chamber and point toward the inlet or upstream end of the chamber. In addition, the two inlet ports 244 and 245 feed into a common injection line 260 coupled in fluid communication with the upstream end of the mixing chamber 250 and extending along the axis or elongated direction of the chamber.

In hematologic applications, a blood sample may be introduced into the first inlet port 244 and diluent may be introduced into the second inlet port 245 to create a diluted blood sample in the common injection line 260 and upstream end of the mixing chamber 250. First and/or second lysing reagents may be simultaneously introduced through the inlet ports 246 and 248, which direct the lysing reagents into the mixing chamber in different directions than the flow of the diluted blood sample, as indicated by the arrows in FIG. 6, thus creating turbulence and facilitating the dispersion and thorough mixing of the components into the reagent-mixture stream to create the selected reagent mixture. As with the previous embodiment, protrusions or like means may be added to the mixing chamber to create further agitation and enhance the dispersion and mixing of the reagent-mixture components.

Figure 7:
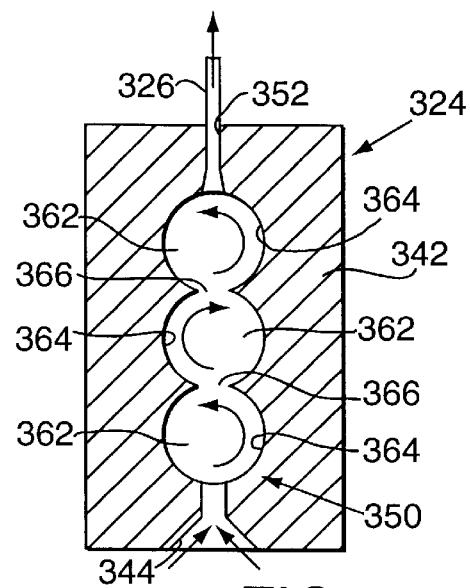
FIG. 7 is a somewhat schematic, cross-sectional view of another embodiment of a flow-injection unit for the apparatus of FIG. 1 having a plurality of diffusion chambers for mixing the reagent-mixture components into the reagent-mixture stream.

In FIG. 7, another embodiment of the flow-injection unit is indicated generally by the reference numeral 324. Because many of the features of the flow-injection unit 324 are the same or similar to those of the flow-injection unit 24 described above, like reference numerals preceded by the numeral 3 are used to indicate like elements.

The primary difference of the mixing block 342 in comparison to the embodiments described above is that it defines a common inlet port 344 on the upstream end of the block for introducing all reagent-mixture components into the mixing chamber 350, and the mixing chamber is defined by a plurality of discrete diffusion chambers 362 extending in seriatim along the axis or elongated direction of the block. As shown in FIG. 7, each diffusion chamber 362 is defined by a substantially spherical wall 364, and relatively constricted apertures 366 are formed between adjacent chambers 362 to permit the reagent mixture to flow from one diffusion chamber to the next.

Upon introduction of the reagent mixture components through the mixing block, the reagent-mixture stream expands and then contracts as it flows through each diffusion chamber 362 and constricted aperture 366, respectively. The expansion and contraction of the flow path in turn causes deceleration and acceleration of the fluid particles as they follow the tortuous path. Accordingly, the reagent-mixture components circulate and disperse within each diffusion chamber, thus causing the components to immediately thoroughly and uniformly mix to create the selected reagent mixture upon passage between the inlet and outlet ports of the mixing block.

Figure 8:
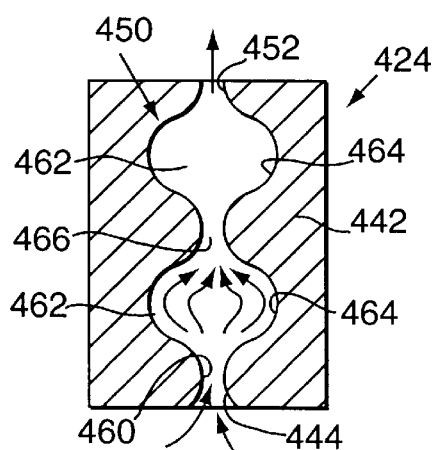
FIG. 8 is a somewhat schematic, cross-sectional view of an alternative embodiment of the flow-injection unit of FIG. 7.

In FIG. 8, an alternative embodiment of the flow-injection unit is indicated generally by the reference numeral 424. The flow-injection unit 424 is essentially the same as the flow-injection unit 324 of FIG. 7, and therefore like reference numeral preceded by the numeral 4 instead of the numeral 3 are used to indicate like elements. The main difference of the mixing block 442 in comparison to the mixing block 342 is that the constricted aperture 466 is relatively elongated, and the surfaces defining the inlet and outlet side of the constricted aperture are curved to facilitate fluid flow through the aperture from the first diffusion chamber 462 to the second. AS will be recognized by those skilled in the pertinent art, in the embodiments of both FIGS. 7 and 8, diffusion chambers may be added or deleted as required to ensure immediate thorough and uniform mixing of the reagent-mixture components.

Figure 9:
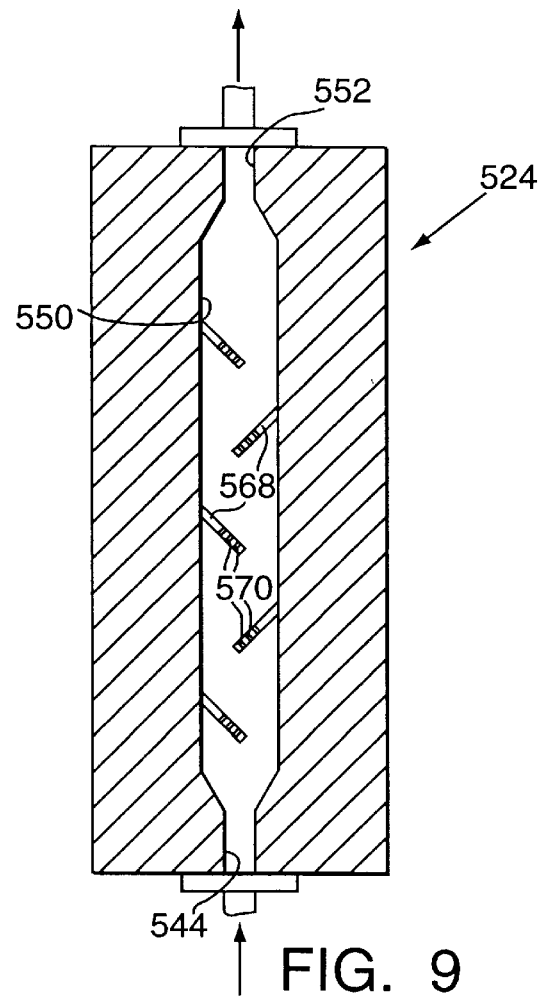
FIG. 9 is a somewhat schematic, cross-sectional view of another embodiment of a flow-injection unit for the apparatus of FIG. 1 having perforated barriers for enhancing the dispersion and mixture of the components in the reagent-mixture stream.

In FIG. 9, another embodiment of the flow-injection unit is indicated generally by the reference numeral 524. Because many of the features of the flow-injection unit 524 are the same or similar to those of the flow-injection unit 24 described above, like reference numerals preceded by the numeral 5 are used to indicate like elements.

The primary difference of the mixing block 542 in comparison to other embodiments described above is that it defines a common inlet port 544 on the upstream end of the mixing block for injecting or aspirating all reagent-mixture components into the mixing chamber 550, and the mixing chamber includes a plurality of perforated barriers or baffles 568. As shown in FIG. 9, each perforated barrier 568 extends inwardly from the cylindrical wall of the chamber to at least approximately the center of the chamber, and is oriented at an acute angle with respect to the axis or elongated direction of the chamber. Each barrier 568 also points generally toward the inlet or upstream end of the mixing chamber 550, and defines a plurality of perforations or apertures 570 spaced relative to each other and extending through the barrier to permit the dispersed flow of reagent-mixture components therethrough. The perforated barriers 568 are spaced relative to each other in the elongated direction of the chamber, i.e., each barrier is located upstream or downstream from the next, and adjacent barriers are preferably spaced radially relative to each other.

Upon introduction of the reagent-mixture components through the common inlet port 544, the perforated barriers 568 cause the reagent-mixture stream to flow around the barriers and through the perforations 570, thereby agitating the fluid flow and creating turbulence. This in turn disperses the reagent-mixture components and thoroughly and uniformly mixes the components to create the selected reagent mixture upon passage from one end of the chamber to the other.

Figure 10:
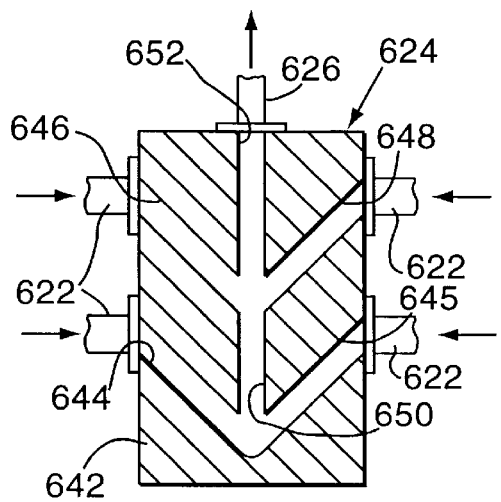
FIG. 10 is a somewhat schematic, cross-sectional view of another embodiment of a flow-injection unit for the apparatus of FIG. 1 wherein the fluid flow through the inlet ports is in generally the opposite direction of fluid flow through the mixing chamber of the unit to create turbulence and facilitate reagent-component mixing.

Turning to FIG. 10, another embodiment of the flow-injection unit is indicated generally by the reference numeral 624. The flow-injection unit 624 is similar in many respects to the flow-injection unit 24 described above, and therefore like reference numerals preceded by the numeral 6 are used to indicate like elements.

As shown in FIG. 10, the mixing chamber 650 is defined by a relatively narrow, cylindrical passageway extending in the axial direction of the mixing block 642, and approximately equal in diameter to the reagent-mixture injection line 626. The mixing chamber 650 defines a closed end at the upstream end of the mixing block and an open end at the downstream end formed by the outlet port 652. As also shown in FIG. 10, the inlet ports 644–648 are each oriented at an acute angle (for example, approximately 45°) relative to the axis of the mixing block 642 and mixing chamber or line 650, and are each directed generally toward the closed or upstream end of the chamber.

In the operation of the flow-injection unit 624 for hematologic analysis, a whole or diluted blood sample may be introduced into the first inlet port 644, diluent may be introduced into the second inlet port 645, a first lysing agent may be introduced into the third inlet port 646, and a second lysing agent may be introduced into the fourth inlet port 648. As indicated by the arrows in FIG. 10, because the sample and diluent are flowing in substantially opposite directions, a turbulent flow is created at the juncture of the first and second inlet ports formed by the closed end of the mixing chamber 650, thus causing the blood and diluent to mix into a diluted blood sample. The pumping pressure at the first and second inlet ports forces the diluted blood sample toward the outlet port 652, and the diluted sample is in turn mixed with the additional reagent-mixture components introduced through the downstream inlet ports 646 and 648. Because the downstream inlet ports are directed generally upstream, the lysing agents are introduced in substantially the opposite direction of flow of the diluted blood sample, thus creating turbulence at the juncture of the downstream inlet ports 646, 648 and the mixing chamber 650, and facilitating an immediate thorough and uniform mixing of the lysing agents into the diluted blood sample. The pumping pressure at each of the inlet ports in turn injects the blood/diluent/lysing agent mixture through the outlet port 652 and into the reagent-mixture injection line 626 for analysis by the sensing unit.

As will be recognized by those skilled in the pertinent art, it may be desirable to space the inlet ports radially relative to each other, and/or axially relative to each other to facilitate or further enhance the immediate diffusion and thorough mixing of the reagent-mixture components.

Figure 12:
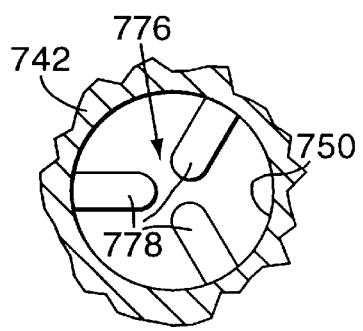
FIG. 12 is a cross-sectional view taken along line 12—12 of FIG. 11 illustrating the means for retaining the mixing ball within the diffusion chamber and permitting fluid flow through the chamber.
Figure 11:
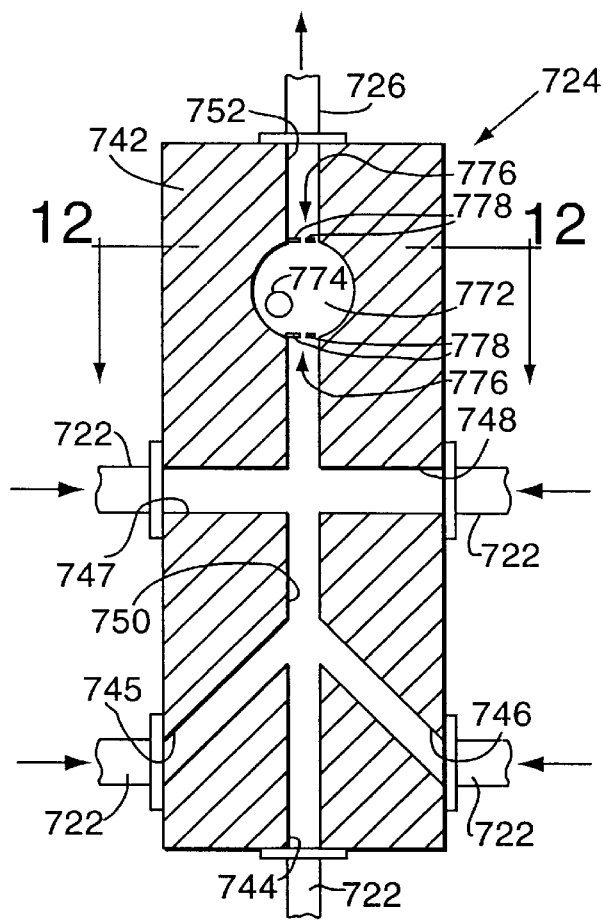
FIG. 11 is a somewhat schematic, cross-sectional view of another embodiment of a flow-injection unit for the apparatus of FIG. 1 having an axially-elongated mixing chamber with a diffusion chamber and mixing ball to facilitate reagent-component mixing.

Turning to FIGS. 11 and 12, another embodiment of the flow-injection unit is indicated generally by the reference numeral 724. The flow-injection unit 724 is similar in many respects to the flow-injection unit 624 described above, and therefore like reference numerals preceded by the numeral 7 instead of the numeral 6 are used to indicate like elements.

As shown in FIG. 11, the mixing chamber 750 is defined by a narrow, cylindrical passageway in the same manner as the mixing chamber 650 described above. However, the upstream end of the mixing chamber 750 is defined by the first inlet port 744, and the downstream end of the mixing chamber is defined by a substantially spherical-shaped diffusion chamber 772. As can be seen, the diffusion chamber 772 defines a greater diameter than does the cylindrical portion of the mixing chamber 750, thus expanding the fluid-flow path to facilitate fluid diffusion and mixing. At least one mixing ball 774 is received within the diffusion chamber 772 to create further turbulence, and enhance the diffusion and thorough mixing of the reagent-mixture components. As will be recognized by those skilled in the pertinent art, additional mixing balls may be added as necessary in order to enhance the dispersion and mixing of the components.

As shown in FIGS. 11 and 12, the flow-injection unit 724 includes means 776 for retaining the mixing ball 774 within the diffusion chamber 772, and for preventing the mixing ball from blocking or otherwise preventing fluid flow through the constricted apertures defined by the upstream and downstream ends of the diffusion chamber. As shown more particularly in FIG. 12, the means 776 may include several prongs 778 radially spaced relative to each other and projecting inwardly toward the center of the constricted aperture to retain the mixing ball while creating turbulence and permitting fluid flow through the diffusion chamber. If desired, screens or other known means may be alternatively employed to perform these functions.

As also shown in FIG. 11, the second and third inlet ports 745 and 746 are each oriented at an acute angle (for example, 45°) relative to the axis of the mixing chamber, and each point generally in the downstream direction. The fourth inlet port 747 and fifth inlet port 748, on the other hand, are each oriented approximately normal to the mixing-chamber axis. In hematologic analysis, the first inlet port 744 may be used to introduce a whole or partially-diluted blood sample, and the second and third inlet ports 745 and 746, respectively, may be used to introduce diluent to further dilute the sample. The fourth and fifth inlet ports 747 and 748, respectively, may in turn be used to introduce respective lysing agents or other reagent-mixture components into the diluted sample stream. Because of the normal configuration of the fourth and fifth inlet ports with respect to the mixing chamber, a greater amount of turbulence is created at the juncture of these ports and the mixing chamber to facilitate immediate and uniform mixing of the reagent-mixture components and provide an even gradient of lytic shock. The reagent-mixture components are then further dispersed and mixed in the diffusion chamber 772 prior to introduction into the reagent-mixture injection line 726.

As will be recognized by those skilled in the pertinent art, numerous modifications may be made to these and other embodiments of the present invention without departing from the scope of the invention as defined in the appended claims. Accordingly, the detailed description of embodiments set forth above is to be taken in an illustrative as opposed to a limiting sense.

What is claimed is:

1. An apparatus for at least one of particle and chemical analysis of reagent mixtures having a plurality of reagent-mixture components, comprising:

means for pumping each of a plurality of reagent-mixture components in a respective stream at a respective flow rate;

means for introducing at least one reagent-mixture component into a stream of at least one other reagent-mixture component to mix the plurality of reagent-mixture components into a combined reagent-mixture stream, said means including an elongated mixing chamber defining an upstream end and a downstream end, at least one inlet port located at the upstream end of the mixing chamber and coupled in fluid communication with the pumping means for introducing a plurality of reagent-mixture component streams into the mixing chamber, an outlet port located downstream of the at least one inlet port for receiving the combined reagent-mixture stream, and a plurality of raised surface portions spaced relative to each other and projecting inwardly into the mixing chamber and transverse relative to its elongated direction for creating turbulence within the mixing chamber to facilitate mixing of the reagent-mixture components into the combined reagent-mixture stream; and means coupled in fluid communication with the outlet port for at least one of (i) chemically analyzing and (ii) analyzing a particle distribution of the combined reagent-mixture stream.

2. An apparatus as defined in claim 1, wherein a first inlet port is aligned with an axis of the mixing chamber for injecting the respective reagent-mixture component on a flow path substantially aligned with the axis of the mixing chamber.

3. An apparatus as defined in claim 1, wherein the mixing chamber is defined by at least one axially-elongated surface extending between the upstream and downstream ends, and the raised surface portions are defined by a plurality of protuberances projecting inwardly from the axially-elongated surface toward approximately the axis of said surface.

4. An apparatus as defined in claim 1, wherein the raised surface portions are at least one of (i) axially spaced relative to each other and (ii) radially spaced relative to each other.

5. An apparatus as defined in claim 1, wherein each raised surface portion defines an axis oriented approximately perpendicular to an elongated axis of the mixing chamber.

6. An apparatus as defined in claim 1, wherein the means for introducing includes an elongated axis extending between the upstream and downstream ends of the elongated mixing chamber, a first inlet port coupled in fluid communication with the pumping means and defining a first inlet axis oriented transverse to the elongated axis of the mixing chamber for introducing a first reagent-mixture component stream into the mixing chamber along the first inlet axis, and a second inlet port angularly spaced relative to the first inlet port, wherein the second inlet port defines a second inlet axis oriented transverse to the elongated axis, and is coupled in fluid communication with the pumping means for introducing a second reagent-mixture component stream into the mixing chamber in a different flow direction than the first reagent-mixture component stream to thereby create turbulence in the combined reagent-mixture stream.

7. An apparatus as defined in claim 1, wherein the means for introducing includes an elongated axis extending between the upstream and downstream ends of the elongated mixing chamber, a first inlet port located at the upstream end of the mixing chamber and coupled in fluid communication with the pumping means, and defining a first inlet axis for introducing a first reagent-mixture component stream into the mixing chamber along the first inlet axis, a second inlet port located downstream of the first inlet port and coupled in fluid communication with the pumping means, and defining a second inlet axis for introducing a second reagent-mixture component stream into the mixing chamber along the second inlet axis, wherein one of the first and second inlet axes is inclined relative to the other and the elongated axis for introducing the respective reagent-mixture component stream into the mixing chamber in a different flow direction than the other reagent-mixture component stream to thereby create turbulence in the combined reagent-mixture stream.

8. An apparatus as defined in claim 1, comprising a plurality of inlet ports, each inlet port being coupled in fluid communication with the mixing chamber either upstream or downstream of an adjacent inlet port.

9. An apparatus as defined in claim 8, wherein each inlet port is coupled in fluid communication with the mixing chamber at a location spaced radially with respect to an adjacent inlet port.

10. An apparatus as defined in claim 1, wherein the mixing chamber defines a diffusion portion and at least one mixing ball received within the diffusion portion for facilitating mixture of the reagent-mixture components.

11. An apparatus as defined in claim 10, wherein the mixing chamber further defines an axially-elongated portion coupled in fluid communication with the diffusion portion.

12. An apparatus as defined in claim 1, wherein the mixing chamber includes a plurality of said raised surface portions and adjacent depressed surface portions forming at least two diffusion chambers and a relatively constricted aperture extending between the diffusion chambers.

13. An apparatus as defined in claim 12, wherein each diffusion chamber is defined by a radial surface.

14. An apparatus as defined in claim 13, wherein the radial surface is substantially spherical.

15. An apparatus as defined in claim 1, wherein the raised surface portions are defined by a plurality of baffles, each baffle projecting inwardly generally toward a central axis of the mixing chamber.

16. An apparatus as defined in claim 15, wherein each baffle defines a plurality of apertures for receiving fluid flow therethrough.

17. An apparatus as defined in claim 15, wherein each baffle also projects generally toward the upstream end of the mixing chamber.

18. An apparatus as defined in claim 1, wherein the raised surface portions are defined by a plurality of tubes, each tube defining a respective inlet port and projecting into the mixing chamber for introducing a respective reagent-mixture component into the mixing chamber.

19. An apparatus as defined in claim 18, wherein each tube defines a plurality of apertures on an end portion projecting into the mixing chamber for introducing the respective reagent-mixture component through the apertures and into the mixing chamber.

20. An apparatus as defined in claim 18, wherein the end portion of each tube projecting into the mixing chamber is oriented generally toward the upstream end of the mixing chamber.

21. An apparatus as defined in claim 18, wherein the tubes are at least one of (i) axially spaced relative to each other and (ii) radially spaced relative to each other.

22. An apparatus as defined in claim 18, wherein each tube is oriented and projects into the mixing chamber in a substantially upstream direction for introducing the respective reagent-mixture component toward a substantially upstream direction.

23. An apparatus as defined in claim 1, further comprising:
   means for forming a plurality of different selected reagent mixtures in the combined reagent-mixture stream, wherein each selected reagent mixture is formed by adjusting the flow rate of at least one of a plurality of reagent-mixture components in accordance with a flow-rate ratio of reagent-mixture components corresponding to the selected reagent mixture.

24. An apparatus as defined in claim 23, further comprising a control unit coupled to the means for pumping and including a database of predetermined reagent-mixture ratios, wherein each predetermined reagent-mixture corresponds to one or more species, and the control unit is responsive to an input for a selected species to control the means for pumping to pump the reagent-mixture components of the respective reagent-mixture ratio of the selected species ay a flow-rate ratio corresponding to the reagent-mixture ratio.

25. An apparatus as defined in claim 23, further comprising a plurality of reagent-mixture component chambers, wherein each reagent-mixture component chamber contains a respective reagent-mixture component and is coupled in fluid communication with the means for pumping for supplying reagent-mixture components to the means for pumping.

26. An apparatus as defined in claim 23, wherein the selected reagent mixture is formed by adjusting the flow rates of at least two reagent-mixture components in accordance with the respective flow-rate ratio.

27. An apparatus as defined in claim 23, wherein the means for pumping includes a plurality of pumps, each pumping a respective reagent-mixture component, and the means for forming the plurality of different selected reagent mixtures is coupled to and controls the flow rate of each pump to in turn control the flow rate of at least one of the plurality of reagent-mixture components in accordance with the flow-rate ratio of the reagent-mixture components corresponding to the selected reagent mixture.

28. An apparatus as defined in claim 27, further comprising a plurality of pump motors, each pump motor being coupled to a respective pump to control the flow rate of the pump and a respective reagent-mixture component.

* * * * *